(12) United States Patent
Igarashi

(10) Patent No.: US 9,804,380 B2
(45) Date of Patent: Oct. 31, 2017

(54) ENDOSCOPE OBJECTIVE OPTICAL SYSTEM

(71) Applicant: OLYMPUS CORPORATION, Hachioji-shi, Tokyo (JP)

(72) Inventor: Tsutomu Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/582,631

(22) Filed: Apr. 29, 2017

(65) Prior Publication Data

US 2017/0235121 A1 Aug. 17, 2017

Related U.S. Application Data

(63) Continuation of application No. PCT/JP2016/064708, filed on May 18, 2016.

(30) Foreign Application Priority Data

May 28, 2015 (JP) ................................ 2015-108613

(51) Int. Cl.
*G02B 13/04* (2006.01)
*G02B 23/24* (2006.01)
(Continued)

(52) U.S. Cl.
CPC ........ *G02B 23/243* (2013.01); *A61B 1/00163* (2013.01); *A61B 1/04* (2013.01); *G02B 9/60* (2013.01); *G02B 13/04* (2013.01)

(58) Field of Classification Search
CPC ........ G02B 23/243; G02B 9/60; G02B 13/04; G02B 23/24; A61B 1/00163; A61B 1/04;
(Continued)

(56) References Cited

U.S. PATENT DOCUMENTS 5,424,877 A * 6/1995 Tsuyuki ............. G02B 23/2407
359/663
2012/0007972 A1 1/2012 Uzawa
(Continued)

FOREIGN PATENT DOCUMENTS

JP 05288986 A 11/1993
JP 07181377 A 7/1995
(Continued)

OTHER PUBLICATIONS

International Search Report (ISR) and Written Opinion dated Jul. 19, 2016 issued in International Application No. PCT/JP2016/064708.

*Primary Examiner* — James Greece
(74) *Attorney, Agent, or Firm* — Holtz, Holtz & Volek PC

(57) ABSTRACT

There is provided an endoscope objective optical system having a thin diameter, a wide in-water angle of view, a small variation in the angle of view, and a short overall length of the optical system.
The endoscope objective optical system includes in order from an object side, a front group GF having a negative refractive power, an aperture stop, and a rear group GR having a positive refractive power, wherein the front group includes a first negative lens L1 and a second negative lens L2, and the following conditional expressions (1), (2), (3'), and (4) are satisfied:

$1 < I_w/f_t < 1.8$ (1), $4 < L_t/I_w < 9.5$ (2), $1.49 \leq L_{sf}/f_t \leq 2.30$ (3'), and $0.38 < \Sigma L_a/L_{sf} < 0.6$ (4).

7 Claims, 6 Drawing Sheets

(51) Int. Cl.
*A61B 1/00* (2006.01)
*A61B 1/04* (2006.01)
*G02B 9/60* (2006.01)

(58) Field of Classification Search
CPC .. A61B 1/00; A61B 8/12; A61B 10/00; A61B 17/32; A61B 18/22; A61B 3/00
USPC .......... 359/753, 754, 749, 763–770
See application file for complete search history.

(56) References Cited

U.S. PATENT DOCUMENTS

| | | |
|---|---|---|
| 2012/0133802 A1 | 5/2012 | Katakura et al. |
| 2015/0309289 A1 | 10/2015 | Nakamura |
| 2015/0359422 A1 | 12/2015 | Igarashi |

FOREIGN PATENT DOCUMENTS

| | | |
|---|---|---|
| JP | 2002014282 A | 1/2002 |
| JP | 2006003549 A | 1/2006 |
| JP | 2012047909 A | 3/2012 |
| WO | 2011070897 A1 | 6/2011 |
| WO | 2011148822 A1 | 12/2011 |
| WO | 2014175038 A1 | 10/2014 |
| WO | 2014208373 A1 | 12/2014 |

* cited by examiner

SA
Fno. 5.528 d LINE

-0.05 , 0.05
(mm)

AS
Iw 0.942

ΔS
ΔM

-0.10 , 0.10
(mm)

DT
Iw 0.942

-100.00 , 100.00
(%)

SA
Fno. 3.78

-0.02　　0.02
(mm)

AS
Iw 0.751

-0.05　　0.05
(mm)

DT
Iw 0.751

-100.00　　100.00
(%)

SA
Fno. 4.761

(mm)

AS
Iw 0.652

(mm)

DT
Iw 0.652

(%)

ENDOSCOPE OBJECTIVE OPTICAL SYSTEM

CROSS-REFERENCE TO RELATED APPLICATION

The present application is a continuation application of PCT/JP2016/064708 filed on May 18, 2016 which is based upon and claims the benefit of priority from Japanese Patent Application No. 2015-108613 filed on May 28, 2015; the entire contents of which are incorporated herein by reference.

BACKGROUND OF THE INVENTION

Field of the Invention

The present invention relates to an endoscope objective optical system, and mainly to an objective optical system for a medical endoscope.

Description of the Related Art

As an endoscope intended for urinary organs, an endoscope (hereinafter, referred to as 'endoscope for urinary organs') having an inserting portion that is to be inserted transurethrally is available. In the endoscope for urinary organs, for letting the inserting portion to be insertable into urethra, it is indispensable to let an outer diameter of the inserting portion to be not more than 7 mm. Therefore, a diameter of the inserting portion of the endoscope for urinary organs is smaller than a diameter of an inserting portion of an endoscope for alimentary tract which is widely known for a medical examination of stomach or large intestine. The urinary organs are generally filled with urine. Therefore, an endoscope objective system used in the endoscope for urinary organs has an optical design envisaged for in-water observation.

In International Unexamined Patent Application Publication No. 2014/208373, an endoscope objective optical system with a wide angle of view at the time of in-water observation (hereinafter, referred to as 'in-water angle of view') has been disclosed. The endoscope objective optical system according to the abovementioned patent literature includes a first group having a negative refractive power, an aperture stop, and a second group having a positive refractive power. In this endoscope objective optical system of International Unexamined Patent Application Publication No. 2014/208373, the in-water angle of view is in a range of 105° to 164°.

Moreover, in International Unexamined Patent Application Publication No. 2014/208373, a medium of an observation space has been described. Here, the observation space is a space for observing urinary organs by the endoscope for urinary organs. In International Unexamined Patent Application Publication No. 2014/208373, it has been signified that the medium of the observation space in this case is a perfusion solution or urine of which water is the main constituent, and that it is reasonable to deem a refractive index of these media to be equivalent to the refractive index of water.

Furthermore, in International Unexamined Patent Application Publication No. 2014/208373, it has been pointed out that the in-water angle of view is narrowed with respect to an angle of view at the time of observation in air (hereinafter, referred to as 'angle of view in air'). Moreover, in International Unexamined Patent Application Publication No. 2014/208373, a relationship of the angle of view in air and the in-water angle of view are shown as follows.

| Angle of view in air | 180° | 160° | 140° | 120° |
|---|---|---|---|---|
| In-water angle of view | 97.2° | 95.3° | 89.7° | 81.0° |

The angle of view in air and in-water angle of view are calculated by letting a refractive index in water for a d-line to be 1.333 and a lens nearest to object in the endoscope objective optical system to be flat.

The abovementioned relationship signifies that even in an endoscope objective optical system with the angle of view in air of 120°, when this endoscope objective optical system is used in an endoscope for urinary bladder, the angle of view at the time of practical use, or in other words, at the time of in-water observation, is narrowed to 81°. In International Unexamined Patent Application Publication No. 2014/208373, a fact that a pathological lesion inside the entire urinary bladder cannot be explored efficiently even with an endoscope objective optical system having a wide angle of view in air has been indicated as an issue.

In Japanese Patent Application Laid-open Publication No. Hei 7-181377, an endoscope objective optical system in which it is possible to switch the angle of view or to reduce a variation in the angle of view has been disclosed. The variation in the angle of view is caused due to a machining accuracy and an assembly error of components. The endoscope objective optical system disclosed in Japanese Patent Application Laid-open Publication No. Hei 7-181377 includes a first group having a negative refractive power, an aperture stop, and a second group having a positive refractive power. A focal length is varied by moving some of the lenses.

In the endoscope objective optical system disclosed in Japanese Patent Application Laid-open Publication No. Hei 7-181377, the angle of view in air is 170° at a wide angle end. In an example 7 of Japanese Patent Application Laid-open Publication No. Hei 7-181377, a positive refractive power is imparted to a front-end surface of the optical system. Accordingly, in the example 7, the in-water angle of view is the widest. The in-water angle of view in the example 7 is 119°. In an endoscope objective optical system of which a front-end surface is flat, given that the in-water angle of view is less than 100° in general, the endoscope objective optical system according to the example 7 of Japanese Patent Application Laid-open Publication No. Hei 7-181377 can be said to be wide-angled even at the time of in-water observation.

In Japanese Patent Application Laid-open Publication No. 2006-3549, an image pickup unit for endoscope in which the variation in the angle of view is reduced has been disclosed. An endoscope objective optical system disclosed in Japanese Patent Application Laid-open Publication No. 2006/3549 includes a first group having a negative refractive power and a second group having a positive refractive power. The angle of view is varied by moving some of the lenses.

In Japanese Patent Application Laid-open Publication No. 2006-3549, the angle of view in air is in a range of 145° to 173°. When converted to the in-water angle of view, in an example in which a front-end surface is flat, the in-water angle of view is less than 100°. Moreover, an example 4 is an example in which the front-end surface has a positive refractive power and the in-water angle of view is the widest, but even in the example 4, the in-water angle of view is 105°.

In Japanese Patent Application Laid-open Publication No. 2002-14282, an endoscope objective optical system in which it is possible to switch the angle of view has been disclosed. The endoscope objective optical system disclosed in Japanese Patent Application Laid-open Publication No. 2002-14282 includes a first group having a negative refractive power, an aperture stop, and a second group having a positive refractive power. Moreover, zooming is carried out moving some of the lenses. The peculiarity of the endoscope objective optical system disclosed in Japanese Patent Application Laid-open Publication No. 200214282 is that at least two negative lenses are disposed in the first group specifically.

In all examples in Japanese Patent Application Laid-open Publication No. 2002-14282, a front-end surface is flat, and the angle of view in air is 138°. Therefore, the angle of view when converted to in-water angle of view is not more than about 89°.

In Japanese Patent Application Laid-open Publication No. 2012-47909, an endoscope objective optical system in which it is possible to switch the angle of view has been disclosed. In the endoscope objective optical system of Japanese Patent Application Laid-open Publication No. 2012-47909, the angle of view in air is not less than 180°. The endoscope objective optical system of Japanese Patent Application Laid-open Publication No. 2012-47909 includes a first group having a negative refractive power, a second group having a negative refractive power, an aperture stop, a third group having a positive refractive power, and a fourth group having a positive refractive power. Zooming is carried out by moving some of the lenses.

In Japanese Patent Application Laid-open Publication No. 2012-47909, the in-water observation has not been explained. However, in all examples, a front-end surface has a positive refractive power. Therefore, an arrangement of the endoscope objective optical system disclosed in Japanese Patent Application Laid-open Publication No. 2012-47909 is advantageous for widening the in-water angle of view. For such reasons, in the endoscope objective optical system of Japanese Patent Application Laid-open Publication No. 2012-47909, it is considered that a sufficiently large in-water angle of view can be secured.

In International Unexamined Patent Application Publication No. 2011/70897, an endoscope objective optical system with a super-wide angle of view has been disclosed. In the endoscope objective optical system disclosed in International Unexamined Patent Application Publication No. 2011-70897, the angle of view in air is not less than 180°. The endoscope objective optical system of International Unexamined Patent Application Publication No. 2011-70897 includes a first group having a negative refractive power, an aperture stop, and a second group having a positive refractive power.

In International Unexamined Patent Application Publication No. 2011-70897, the in-water observation has not been explained. However, in all examples, a front-end surface has a positive refractive power. Therefore, an arrangement of the endoscope objective optical system of International Unexamined Patent Application Publication No. 2011-70897 is advantageous for widening the in-water angle of view. For such reasons, in the endoscope objective optical system of International Unexamined Patent Application Publication No. 2011-70897, it is considered that a sufficiently large in-water angle of view can be secured.

In International Unexamined Patent Application Publication No. 2011/148822, an endoscope objective optical system with a super-wide angle of view has been disclosed. In the endoscope objective optical system disclosed in International Unexamined Patent Application Publication No. 2011/148822, the angle of view in air is not less than 180°. The endoscope objective optical system of International Unexamined Patent Application Publication No. 2011/148822 includes a first group having a negative refractive power, an aperture stop, and a second group having a positive refractive power.

In International Unexamined Patent Application Publication No. 2011/148822, the in-water observation has not been explained. However, in all examples, a front-end surface has a positive refractive power. Therefore, an arrangement of the endoscope objective optical system of International Unexamined Patent Application Publication No. 2011/148822 is advantageous for widening the in-water angle of view. For such reasons, in the endoscope objective optical system disclosed in International Unexamined Patent Application Publication No. 2011/148822, it is considered that a sufficiently large in-water angle of view can be secured.

In Japanese Patent Application Laid-open Publication No. Hei 5-288986 envisaging the in-water observation has been disclosed. However, even in examples (6 to 9, 17, and 18) in which the angle of view in air is the largest, the angle of view is 138.3°. This angle of view when converted to the in-water angle of view is 89°.

SUMMARY OF THE INVENTION

An endoscope objective optical system according to the present invention comprises in order from an object side, a front group having a negative refractive power, an aperture stop, and a rear group having a positive refractive power, wherein the front group includes a first negative lens and a second negative lens, and the following conditional expressions (1), (2), (3'), and (4) are satisfied:

$$1 < Iw/ft < 1.8 \quad (1),$$

$$4 < Lt/Iw < 9.5 \quad (2),$$

$$1.49 \leq Lsf/ft \leq 2.30 \quad (3'), \text{ and}$$

$$0.38 < \Sigma La/Lsf < 0.6 \quad (4)$$

where,

Iw denotes a maximum image height, ft denotes a focal length of the overall endoscope objective optical system, Lt denotes an overall length of the endoscope objective optical system, Lsf denotes a distance from an object-side first surface up to the aperture stop, and $\Sigma La$ denotes a sum of air spaces between the object-side first surface and the aperture stop, and in this case, the overall length is a distance from the object-side first surface up to an image position, and the object-side first surface is a lens surface positioned nearest to object in the endoscope objective optical system.

Moreover, another endoscope objective optical system according to the present invention comprises in order from an object side, a front group having a negative refractive power, an aperture stop, and a rear group having a positive refractive power, wherein the front group includes a first negative lens and a second negative lens, and the rear group includes a first positive lens, a second positive lens, and a cemented lens, and the cemented lens includes a lens having a positive refractive power and a lens having a negative refractive power, and the following conditional expressions (1), (2), (3'), and (4) are satisfied:

$$1 < Iw/ft < 1.8 \quad (1),$$

$$4 < Lt/Iw < 9.5 \quad (2),$$

$$1.49 \leq Lsf/ft \leq 2.30 \quad (3'), \text{ and}$$

$$0.38 < \Sigma La/Lsf < 0.6 \quad (4),$$

where,

Iw denotes a maximum image height, ft denotes a focal length of the overall endoscope objective optical system, Lt denotes an overall length of the endoscope objective optical system, Lsf denotes a distance from an object-side first surface up to the aperture stop, and ΣLa denotes a sum of air spaces between the object-side first surface and the aperture stop, and in this case, the overall length is a distance from the object-side first surface up to an image position, and the object-side first surface is a lens surface positioned nearest to object in the endoscope objective optical system.

BRIEF DESCRIPTION OF THE DRAWINGS

FIG. 2A shows a first arrangement and FIG. 2B shows a second arrangement;

FIG. 6A is a diagram showing an image pickup range in an in-water observation state and FIG. 6B is a diagram showing an image pickup range in a state of observation in air.

DETAILED DESCRIPTION OF THE INVENTION

Reasons for adopting such arrangements and effects thereof in an endoscope objective optical system according to the present embodiment will be described below by referring to the accompanying diagrams. However, the present invention is not limited to the following endoscope objective optical system according to the present embodiments.

A basic arrangement of an endoscope objective optical system according to an embodiment will be described below. The optical system with the basic arrangement includes in order from an object side, a front group having a negative refractive power, an aperture stop, and a rear group having a positive refractive power, and the front group includes a first negative lens and a second negative lens.

The endoscope objective optical system according to the present embodiment is a super-wide angle optical system. Therefore, in the endoscope objective optical system of the present embodiment, in order to secure an extremely wide angle of view, a so-called retro-focus type arrangement which is most appropriate for widening the angle of view has been adopted as the basic arrangement.

Figure 1:
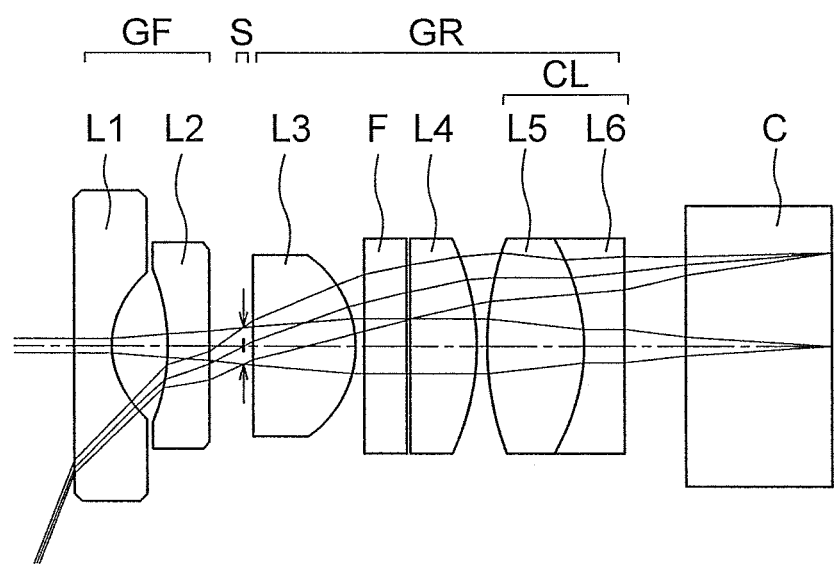
FIG. 1 is a diagram showing a basic arrangement of an endoscope objective optical system according to the present embodiment.

In FIG. 1, an example of the basic arrangement of the endoscope objective optical system according to the present embodiment is shown. In the basic arrangement, the optical system includes in order from an object side a front group GF having a negative refractive power, an aperture stop S, and a rear group GR having a positive refractive power.

Furthermore, in the basic arrangement, the front group GF includes a first negative lens L1 and a second negative lens L2. Both the first negative lens L1 and the second negative lens L2 are single lenses. Thus, by restricting the lenses in the front group GF to two negative single lenses, in a space on the object side of the aperture stop S, a structure having no contribution to widening of angle, shortening of an entrance pupil position, and adjustment of the angle of view is eliminated. Shortening of the entrance pupil position means to bring the entrance pupil position closer to the object side.

The endoscope objective optical system according to the present embodiment can also be used for observing urinary organs. As aforementioned, the urinary organs are to be observed in water. For securing a wide angle of view at the time of in-water observation, the negative refractive power is not adequate in a case where the front group GF consists of one negative lens in. Therefore, by including two negative lenses in the front group GF, the negative refractive power is secured adequately. As a result, it is possible to secure a wide angle of view for the in-water observation.

When either the first negative lens L1 or the second negative lens L2 in the front group GF is made to be a cemented lens, or both of the first negative lens L1 and the second negative lens L2 are made to be a cemented lens, due to an increase in a lens thickness, a space on the object side of the aperture stop S becomes long. By letting each of the first negative lens L1 and the second negative lens L2 to be a single lens, it is possible to avoid the increase in the lens thickness. As a result, it is possible to minimize a space occupied by the lens in the space on the object side of the aperture stop S.

Such arrangement of the front group GF realizes the shortening of length of the front group and contributes to shortening the overall length of the optical system.

In such manner, in the basic arrangement of the endoscope objective optical system according to the present embodiment, each of the thinning of diameter (making a lens outer diameter small), widening of angle, and shortening the overall length of the optical system has been taken into consideration.

An optical system in which a positive lens is disposed on the object side of an aperture stop S is one of the super-wide angle optical systems. However, the positive refractive power disposed in the front group GF has an effect of narrowing the angle of view. Furthermore, as the positive refractive power positions an entrance pupil position further on an image side, it increases the lens outer diameter. Therefore, it is not desirable to dispose the positive lens on the object side of the aperture stop S.

The aperture stop S is disposed between the front group GF and the rear group GR. In a case in which a space between the front group GF and the rear group GR is narrow, the aperture stop S may be provided to a lens surface. As a method for providing the aperture stop S to the lens surface, a method of coating the lens surface by a metallic light-shielding film and forming an aperture by etching, and a method of pinching a thin annular metallic plate between a lens and a frame are available.

The rear group GR includes a first positive lens L3, a second positive lens L4, and a cemented lens CL. The cemented lens CL includes a positive lens L5 and a negative lens L6. Moreover, an optical filter F is disposed in the rear group GR. In FIG. 1, the optical filter F is disposed between the first positive lens L3 and the second positive lens L4.

The optical filter F is a filter such as an infra-red cut filter or a conversion filter for color temperature. These filters are to be used for correcting sensitivity of an image pickup element such as a CCD (charge coupled device).

Moreover, a laser cut filter or a special feature filter may be disposed in the optical system. An example of the laser cut filter is a filter for cutting laser light of YAG (Yttrium Aluminum Garnet) laser or semiconductor laser. An example of the special feature filter is a notch filter which cuts light rays of a specific wavelength region.

Moreover, for the optical filter F, an absorption-type filter or a reflection-type filter, or a composite-type filter in which the absorption-type filter and the reflection-type filter are combined, may be used. Moreover, a filter having an anti-reflection film applied thereto may be used.

A glass block C is disposed on the image side of the rear group GR. The glass block C is a component designed assuming a cover glass of a solid image pickup element. An image of an object having an image height Iw is formed on an image-side surface of the glass block C. The image-side surface of the glass block C matches with an image pickup surface of an image pickup element.

An endoscope objective optical system according to a first embodiment and an endoscope objective optical system according to a second embodiment will be described below.

The endoscope objective optical system according to the first embodiment has the abovementioned basic arrangement, and the following conditional expressions (1), (2), (3), and (4) are satisfied:

$$1 < Iw/ft < 1.8 \quad (1),$$

$$4 < Lt/Iw < 9.5 \quad (2),$$

$$Lsf/ft < 2.8 \quad (3), \text{ and}$$

$$0.38 < \Sigma La/Lsf < 0.6 \quad (4),$$

where,

Iw denotes a maximum image height, ft denotes a focal length of the overall endoscope objective optical system, Lt denotes an overall length of the endoscope objective optical system, Lsf denotes a distance from an object-side first surface up to the aperture stop, and $\Sigma La$ denotes a sum of air spaces between the object-side first surface and the aperture stop, and in this case, the overall length is a distance from the object-side first surface up to an image position, and the object-side first surface is a lens surface positioned nearest to object in the endoscope objective optical system.

Conditional expression (1) is a conditional expression related to the in-water angle of view. For the maximum image height Iw, the in-water observation is also taken into consideration. Here, ft is the focal length of the overall endoscope objective optical system. However, in a case in which the object-side first surface has a curvature, the focal length varies according to a refractive index of an object-side medium. Therefore, ft is let to be a focal length when the object-side medium is let to be air similarly as in a definition of focal length of a lens in general.

In conditional expression (1), as a value of Iw/ft becomes small, the in-water angle of view becomes narrow, and as the value of Iw/ft becomes large the in-water angle of view becomes wide.

In a conventional endoscope objective optical system designed for observation in air, an image height H is basically proportional to sine of an angle of incidence $\theta$ and the focal length ft in many cases. Such endoscope objective optical system has been known as an objective optical system of a so-called $H = ft \times \sin(\theta a)$ type. In this case, $\theta a$ an angle made by a principal ray with an optical axis in an object-side medium space, and is an angle at the time of observation in air. In the objective optical system of $H = ft \times \sin(\theta a)$ type, a value of H/ft becomes not less than 1.

Whereas, in the endoscope objective optical system of the first embodiment, a value of Iw/ft becomes larger than 1 as evident from conditional expression (1). This signifies that in the endoscope objective optical system according to the first embodiment, the maximum image height at the time of in-water observation is secured to be larger than the image height assumed at the time of observation in air. Exceeding a lower limit value of conditional expression (1) contributes to widening of the in-water angle of view. By making so as to fall below an upper limit value of conditional expression (1), it is possible to avoid excessive widening of the in-water angle of view.

In a case of falling below the lower limit value of conditional expression (1), the in-water angle of view becomes narrow. In other words, it becomes difficult to secure adequately the angle of view necessary for observation in water.

In a case of exceeding the upper limit value of conditional expression (1), the in-water angle of view becomes excessively wide. In this case, there is a degradation of brightness in a peripheral portion of a field of view of observation and a peripheral portion of an image acquired by an image pickup element. Therefore, it is not desirable to exceed the upper limit value of conditional expression (1). Examples of degradation of brightness in the peripheral portion of the field of view and the peripheral portion of image are inadequate light distribution at an illuminating optical system side or degradation of peripheral brightness in an objective optical system.

Conditional expression (2) is a conditional expression related to the overall length of the optical system. Here, Lt/Iw signifies that the overall length of the optical system is standardized at the maximum image height. Smaller a value of Lt/Iw, it is possible to realize the endoscope objective optical system having a short overall length of the optical system. The maximum image height may be deemed to be almost proportional to a size of an image pickup surface of the solid image pickup element.

In a case of falling below a lower limit value of conditional expression (2), the overall length of the optical system becomes excessively short. As a result, it becomes difficult to secure a space necessary for the correction of angle of view and to secure an adequate aberration correction and ease at the time of manufacturing of lens and. Therefore, it is not desirable to fall below the lower limit value of conditional expression (2).

In a case of exceeding an upper limit value of conditional expression (2), a length of a front-end hard portion increases. If the length of the front-end hard portion is long, a distance up to an object becomes short when a front-end portion of endoscope is curved. As a result, since the field of view is narrowed, the worth of widening the field of view by widening the angle is declined. Therefore, it is not desirable to exceed the upper limit value of conditional expression (2).

Conditional expression (3) is a conditional expression related to the maximum diameter of a lens. Generally, among wide angle lenses, a so-called front-cell lens is a lens having the maximum diameter. In the endoscope objective optical system according to the first embodiment, a lens having the object-side first surface, or in other words the first negative lens, corresponds to the front-cell lens.

In a super-wide angle lens, a light-ray height at the first negative lens is almost determined by the angle of view and the entrance pupil position. When the angle of view is set, the entrance pupil position becomes a parameter which determines the light-ray height at the first negative lens. Farther the entrance pupil position toward the image side from the object-side first surface, higher is the light-ray height at the first negative lens. Therefore, for making a diameter of the first negative lens small, it is necessary to devise an idea to bring the entrance pupil position closer to the object-side first surface.

For bringing the entrance pupil position closer to the object-side first surface, a distance from the object-side first surface up to the aperture stop (hereinafter, referred to as 'Lsf') is to be shortened. Therefore, Lsf is standardized by the focal length of the overall endoscope objective optical system (hereinafter, referred to as 'ft'), and an upper limit value is set. In conditional expression (3), Lsf is standardized by ft and not by the maximum image height. The reason for doing so is that a factor of the angle of view is also to be taken into account as a condition.

For instance, when the maximum image height is let to be determined by the size of the image pickup surface of the image pickup element, the maximum image height does not include the factor of the angle of view. Whereas, regarding ft, when the maximum image height is let to be constant, a relationship that as the value of ft becomes small, the angle of view becomes wide is established. Thus, ft is included in the factor of the angle of view.

By standardizing Lsf by ft, as the value of ft becomes smaller with the widening of angle, an upper limit value of Lsf also becomes small. As a result, it is possible to regulate an outer diameter of the first negative lens more strictly.

In a case of exceeding an upper limit value of conditional expression (3), the outer diameter of the first negative lens increases. With the increase in the outer diameter of the first negative lens, a diameter of the endoscope, particularly a diameter of the front-end hard portion, becomes thick. Therefore, it is not preferable to exceed the upper limit value of conditional expression (3).

For changing the angle of view, it is preferable to change the focal length of the overall optical system. However, it is necessary to make small a distance of lens movement and a variation in focus with a variation of the focal length. In an optical system of retro-focus type, by changing a distance between a lens group having a negative refractive power and a lens group having a positive refractive power, it is possible to change the focal length substantially while maintaining the variation in focus and the distance of movement to be small. Therefore, in the optical system of retro-focus type, it is favorable to adjust the angle of view by changing the distance between the lens group having a negative refractive power and a lens group having a positive refractive power.

Conditional expression (4) is a conditional expression related to the adjustment of the angle of view. For carrying out the adjustment of the angle of view, it is necessary to select the distance at which the focal length can be changed substantially while maintaining the variation in focus and the distance of movement to be small, and to change the distance by the movement of lens. As aforementioned, in the basic arrangement, the arrangement of retro-focus type is adopted. In the endoscope objective optical system according to the first embodiment, a boundary of the negative refractive power and the positive refractive power is between the first negative lens and the second negative lens or between the second negative lens and the aperture stop. Therefore, the distance between the first negative lens and the second negative lens or the distance between the second negative lens and the aperture stop becomes a distance preferable for the adjustment of the angle of view.

An endoscope objective optical system includes optical elements such as a lens and optical filter. For disposing these optical elements at distances determined in advance, it is preferable to hold optical elements divided into a plurality of groups by respective frame members, and to adjust positions of the frame member. While doing so, there is a variation in dimensions of each component such as the optical element and frame member due to a manufacturing error. Consequently, sometimes, according to a combination of components, the angle of view at a wide-angle end of the endoscope objective optical system becomes excessively wide beyond an acceptable range that has been set in advance.

As aforementioned, in the optical system of retro-focus type, the angle of view is adjusted by changing the distance at the boundary of the negative refractive power and the positive refractive power. In this case, for containing the excessively wide angle of view in a predetermined acceptable range, it is necessary to reduce the distance at the boundary. For such reason, in order to carry out adequately the adjustment of the angle of view by reducing the distance, it is significant to secure a substantial range for the lens movement.

In the endoscope objective optical system according to the first embodiment, by satisfying conditional expression (3), a space on the object side of the aperture stop is made as narrow as possible. Therefore, it is necessary to secure an air space in the limited space with an appropriate proportion.

Here, $\Sigma La/Lsf$ indicates a proportion of the air space between the object-side first surface and the aperture stop with respect to the distance between the object-side first surface and the aperture stop. In a case in which the first negative lens and the second negative lens are the only optical members positioned on the object side of the aperture stop, $\Sigma La$ becomes a sum of the air space between the first negative lens and the second negative lens and the air space between the second negative lens and the aperture stop.

In a case of falling below a lower limit value of conditional expression (4), the proportion of the air space becomes excessively small. In this case, a sufficient range for the adjustment of the angle of view cannot be secured. Particularly, in a case in which the endoscope objective optical system includes a combination of components that cause an excessive variation on a wide angle side, the angle of view cannot be narrowed adequately. Therefore, it is not desirable to fall below the lower limit value of conditional expression (4).

In a case of exceeding an upper limit value of conditional expression (4), the proportion of the air space becomes excessively large. In this case, a thickness of the first negative lens and the second negative lens cannot be secured adequately. As a result, strength-related issues, such as damage at the time of machining the first negative lens and the second negative lens and damage after the assembling in a frame, arise. Therefore, it is not desirable to exceed the upper limit value of conditional expression (4).

It is preferable to select the location for the adjustment of the angle of view from either between the first negative lens and the second negative lens or between the second negative lens and the aperture stop, upon satisfying conditional expression (4). For a small-size lens frame to be mounted in an endoscope, it is significant to take into account the requirements at the time of designing the lens frame, such as a workability of a frame component, assemblability, and a reliable quality. The selection of the location for the adjustment of the angle of view has a strong effect on a lens-frame design. Therefore, for the selection of the location for the adjustment of the angle of view, it is desirable to select a location where it is easy to secure the range for adjustment upon satisfying the requirements for the lens-frame design.

Moreover, in the endoscope objective optical system according to the first embodiment, it is preferable that the rear group include on the object side a first positive lens and a second positive lens, and the following conditional expressions (5) and (6) are satisfied:

$$0.25 < PSp12 \times ft \quad (5), \text{ and}$$

$$0.5 < |PSp12/PSn12| < 1.1 \quad (6)$$

where, ft denotes the focal length of the overall endoscope objective optical system, PSp12 denotes Petzval sum for the first positive lens and the second positive lens, and PSn12 denotes Petzval sum for the first negative lens and the second negative lens.

Both of conditional expression (5) and conditional expression (6) are conditional expressions related to a partial Petzval sum. Petzval sum which serves as a measure of a curvature of field, is a sum of a refractive power at a boundary surface formed by two areas making a contact divided by a refractive index of an area positioned on both sides of the boundary, and has a dimension of a reciprocal of length. The Petzval sum can be calculated for each boundary surface. Therefore, in the optical system, according to the number of lens surfaces subjected to calculation, the partial Petzval sum can be calculated for each lens or for each lens group.

As aforementioned, in the endoscope objective optical system according to the first embodiment, the arrangement of retro-focus type is adopted for the basic arrangement. When the optical system of retro-focus type is let to have a super-wide angle, since a front group has a large negative refractive power, Petzval sum in the front group becomes negative. As a result, the curvature of field which tends to have an excessive correction is susceptible to occur. For correcting this in the overall optical system, it is necessary to ingenerate a large positive Petzval sum in the rear group, and to achieve a balance with the negative Petzval sum generated in the front group.

In the arrangement of retro-focus type, a light beam is diverged substantially at the front group, and substantially diverged light beam is incident on the rear group. Therefore, it is necessary to dispose a lens having a large positive refractive power on the object side in the rear group, and to convert the light beam into a converged direction toward the object side in the rear group. In such manner, it is efficient to cancel the negative Petzval sum generated in the front group by using the lens having a positive refractive power disposed on the object side in the rear group and the refractive index of the lens.

In the endoscope objective optical system according to the first embodiment, the first positive lens and the second positive lens are disposed in the rear group, and the two positive lenses are let to have a large positive value of Petzval sum. In the endoscope objective optical system, shortening of the overall length of the optical system is desired. Therefore, a space in which lenses are disposed in the optical system is limited. For ingenerating efficiently the positive Petzval sum in this limited space, it is desirable to let the first positive lens and the second positive lens to be single lenses rather than cemented lenses, and furthermore, it is desirable to satisfy conditional expression (5) by selecting the refractive power and the refractive index of each positive lens.

Conditional expression (5) is a conditional expression related to Petzval sum for the first positive lens and the second positive lens (hereinafter, referred to as 'PSp12'), and is let to be dimensionless by multiplying PSp12 by ft, and also standardized.

In a case of falling below a lower limit value of conditional expression (5), the positive Petzval sum in the rear group becomes excessively small. Therefore, when the positive Petzval sum is to be used for cancelling the negative Petzval sum in the front group, the positive Petzval sum is absolutely inadequate. Therefore, it is not desirable to fall below the lower limit value of conditional expression (5).

Conditional expression (6) is a conditional expression related to balance of the aforementioned PSp12 and Petzval sum of the front group (hereinafter, referred to as 'PSn12'). In the endoscope objective optical system according to the present embodiment, it is desirable to let an absolute value of PSn12 as small as possible. However, the refractive power of the front group is almost determined by the angle of view and an outer diameter of lenses. Therefore, the only freedom for making the absolute value of PSn12 small is a freedom to use a material having a high refractive index for the first negative lens and the second negative lens.

For such reasons, practically, PSn12 remains to be present substantially as the absolute value. Therefore, a balance is to be taken by intentionally ingenerating PSp12 of a large value with respect to PSn12 having a large value. Since a sign for the value of PSp12 and a sign for the value of PSn12 being different, in conditional expression (6), a ratio of the two is taken in absolute values.

When a value of |PSp12/PSn12| is 1, it is a state in which Petzval sums are cancelled by these four lenses. Therefore, from a viewpoint of Petzval sum, it is possible to realize a favorable endoscope objective optical system.

In a case of falling below a lower limit value of conditional expression (6), PSp12 becomes excessively small relatively with respect to PSn12. In this case, the negative Petzval sum cannot be cancelled adequately by the positive Petzval sum. As a result, the Petzval sum in the overall endoscope objective optical system remains in a state of being excessively corrected. Therefore, it is not desirable to fall below the lower limit value of conditional expression (6).

Incidentally, in endoscope for observing inside of a lumen, an object in a periphery of field of view is susceptible to come close to the endoscope objective optical system. Therefore, when correction of the curvature of field tends to be slightly inadequate, the periphery of the field of view is susceptible to come into focus. On the other hand, in a case in which the curvature of field for which the correction tends to be excessive has remained, the focus in the periphery of the field of view is let to be blurred further. Therefore, it is not preferable that the curvature of field for which the correction tends to be excessive, remains.

In a case of exceeding an upper limit value of conditional expression (6), PSp12 becomes larger than necessary. In this case, the first positive lens and the second positive lens are to be made of a material having a low refractive index, and an extremely large positive refractive power is to be imparted to the two positive lenses. However, when such an arrangement is made, the manufacturing error sensitivity such as decentering becomes excessively high. In general, decentering deteriorates an imaging performance either by deforming a shape of a point spread function or by deteriorating symmetry of an image plane and flatness. High manufacturing error sensitivity of decentering leads to susceptibility to deterioration of the imaging performance at the time of mounting. Therefore, it is not desirable to make PSp12 larger than necessary, or in other words, to exceed 1.1 which is the upper limit value of conditional expression (6).

Moreover, in the endoscope objective optical system according to the first embodiment, it is preferable that the rear group have a cemented lens on the image side of the second positive lens, and the cemented lens include a lens having a positive refractive power and a lens having a negative refractive power, and the following conditional expression (7) be satisfied:

$$0.02 < PS3 \times ft \quad (7)$$

where, ft denotes the focal length of the overall endoscope objective optical system, and PS3 denotes Petzval sum for the cemented lens.

With the four lenses namely, the first negative lens, the second negative lens, the first positive lens, and the second positive lens, realization of desired specifications and a favorable correction of the curvature of field are possible by and large. However, with these four lenses only, favorable correction of a spherical aberration, a coma, an astigmatism, and a chromatic aberration is not carried out thoroughly.

Therefore, a cemented lens made of a combination of a lens having a positive refractive power and a lens having a negative refractive power is to be added in the rear group. By doing so, correction of the spherical aberration, the coma, the astigmatism, and the chromatic aberration becomes possible.

For the lens having a negative refractive power, it is preferable to use a glass material with a high refractive index and a high dispersion, and for the lens having a positive refractive power, it is preferable to use a glass material having a relatively lower refractive index and lower dispersion than that of the glass material used for the lens having a negative refractive power. Such a combination is used quite often normally.

However, in order to avoid as far as possible the correction of the curvature of field from tending to be excessive, in the endoscope objective optical system according to the first embodiment, a condition related to Petzval sum is added to the cemented lens as well.

Conditional expression (7) is a conditional expression in which Petzval sum of the cemented lens is multiplied by ft and let to be dimensionless, and also standardized. By satisfying conditional expression (7), the Petzval sum for the cemented lens can be used for cancelling the negative Petzval sum for the front group. As a result, this leads to an improvement in Petzval sum for the overall endoscope objective optical system. Moreover, as aforementioned, the restriction on the first positive lens and the second positive lens is susceptible to be traded off for a deterioration of image quality due to manufacturing error. Satisfying conditional expression (7) may as well relax the restriction on the first positive lens and the second positive lens.

In a case of falling below a lower limit value of conditional expression (7), the abovementioned effect cannot be achieved. Therefore, it is not desirable to fall below the lower limit value of conditional expression (7).

An endoscope objective optical system according to a second embodiment includes in order from an object side, a front group having a negative refractive power, an aperture stop, and a rear group having a positive refractive power, and the front group includes a first negative lens and a second negative lens, and the rear group includes a first positive lens, a second positive lens, and a cemented lens, and the cemented lens includes a lens having a positive refractive power and a lens having a negative refractive power, and the following conditional expressions (1), (2), (3), and (4) are satisfied:

$$1 < Iw/ft < 1.8 \quad (1)$$

$$4 < Lt/Iw < 9.5 \quad (2),$$

$$Lsf/ft < 2.8 \quad (3), \text{ and}$$

$$0.38 < \Sigma La/Lsf < 0.6 \quad (4)$$

where,

Iw denotes a maximum image height, ft denotes a focal length of the overall endoscope objective optical system, Lt denotes an overall length of the endoscope objective optical system, Lsf denotes a distance from an object-side first surface up to the aperture stop, and ΣLa denotes a sum of air spaces between the object-side first surface and the aperture stop, and in this case, the overall length is a distance from the object-side first surface up to an image position, and the object-side first surface is a lens surface positioned nearest to object in the endoscope objective optical system.

Moreover, in the endoscope objective optical system according to the second embodiment, it is preferable that the following conditional expressions (5), (6), and (7) be satisfied:

$$0.25 < PSp12 \times ft \quad (5),$$

$$0.5 < |PSp12/PSn12| < 1.1 \quad (6), \text{ and}$$

$$0.02 < PS3 \times ft \quad (7)$$

where, ft denotes the focal length of the overall endoscope objective optical system, PSp12 denotes Petzval sum for the first positive lens and the second positive lens, PSn12 denotes Petzval sum for the first negative lens and the second negative lens, and PS3 denotes Petzval sum for the cemented lens.

Since arrangements and conditional expressions for the endoscope objective optical system according to the second embodiment have been described in the endoscope objective optical system according to the first embodiment, description thereof will be omitted here.

Moreover, in the endoscope objective optical system according to the first embodiment and the endoscope objective optical system according to the second embodiment (hereinafter, referred to as 'endoscope objective optical system according to the present embodiment'), it is preferable that the first negative lens be a planoconcave lens of which an object-side surface is a flat surface.

By letting the object-side surface to be a flat surface, it is possible to reduce a damage to the lens surface. Moreover, since water droplets are not susceptible to accumulate on a peripheral portion of the lens surface, there is no narrowing of an observable range.

Moreover, in the endoscope objective optical system according to the present embodiment, it is preferable that the refractive index of the first negative lens be not less than 1.75.

By making such arrangement, it is possible to make the outer diameter of the first negative lens small.

Moreover, in the endoscope objective optical system according to the present embodiment, it is preferable that a glass material for the first negative lens be sapphire.

Sapphire being an extremely hard material is strong against an external impact. Therefore, the object-side lens surface is not susceptible to be scratched. By using sapphire, projection of scratch on image, and a flare due to the scratch are not susceptible to occur.

Moreover, in the endoscope objective optical system according to the present embodiment, it is preferable that an object-side surface of the second negative lens be a concave surface directed toward the object side.

In the endoscope objective optical system according to the present embodiment, it is preferable that the second negative lens be a planoconcave lens, and have a concave surface directed toward the object side, and an image-side surface of the second negative lens be a flat surface.

Moreover, in the endoscope objective optical system according to the present embodiment, it is preferable that a refractive index of the second negative lens be not less than 1.75.

Furthermore, in the endoscope objective optical system according to the present embodiment, it is preferable that an image-side surface of the first positive lens be a convex surface directed toward the image side.

In the endoscope objective optical system according to the present embodiment, it is preferable that the first positive lens be a planoconvex lens of which an object-side surface be a flat surface, and an image-side surface be a convex surface directed toward the image side.

Moreover, in the endoscope objective optical system according to the present embodiment, it is preferable that a refractive index of the first positive lens be less than 1.75.

Furthermore, in the endoscope objective optical system according to the present embodiment, it is preferable that an image-side surface of the second positive lens be a convex surface directed toward the image side.

In the endoscope objective optical system according to the present embodiment, it is preferable that the second positive lens be a planoconvex lens of which an object-side surface be a flat surface, and an image-side surface be a convex surface directed toward the image side.

Moreover, in the endoscope objective optical system according to the present embodiment, it is preferable that a refractive index of the second positive lens be higher than the refractive index of the first positive lens.

Furthermore, in the endoscope objective optical system according to the present embodiment, it is preferable that the lens having a positive refractive power in the cemented lens be a biconvex lens.

In the endoscope objective optical system according to the present embodiment, it is preferable that a refractive index of a concave lens be not less than 1.85, and Abbe number for the concave lens be not more than 23.

Next, an endoscope objective unit according to the present embodiment will be described below. The endoscope objective unit according to the present embodiment includes an endoscope objective optical system, a first holding member, and a second holding member, wherein the endoscope objective optical system includes in order from an object side, a first negative lens, a second negative lens, a first positive lens a second positive lens, and a cemented lens, and the first holding member has at least the first negative lens, the second holding member has at least the first positive lens, the second positive lens, and the cemented lens, and the first holding member and the second holding member are moved relatively along an optical axis.

As aforementioned, the endoscope objective optical system includes optical elements such as a lens and an optical filter. For disposing these optical elements at distances determined in advance, it is preferable to hold optical elements divided into a plurality of groups by respective frame members, and to adjust positions of the frame members are. A unit in which all the optical members are held by frame members, and the frame members are in a state of being combined is let to be the endoscope objective unit in this case.

Various adjustments are made while assembling the endoscope objective unit. One of the adjustments is an adjustment of the angle of view of the optical system. In a super-wide angle optical system, the angle of view is extremely wide. Therefore, the adjustment of the angle of view in the super-wide angle optical system becomes extremely difficult task. The angle of view can be adjusted by changing a focal length of the optical system.

As aforementioned, in the arrangement of retro-focus type, by changing the distance between the lens group having a negative refractive power and the lens group having a positive refractive power, it is possible to change substantially the focal length while maintaining the variation in focus and the distance of movement to be small. In the endoscope objective optical system according to the present embodiment, the arrangement of retro-focus type has been adopted as the basic arrangement. Therefore, even in the endoscope objective unit according to the present embodiment, it is possible to adjust the angle of view by a small change in distance, by changing a distance between the front group and the rear group.

As aforementioned, in the basic arrangement, the front group GF includes two negative lenses, and the two negative lenses are disposed to be independent. Therefore, there is an arrangement in which one negative lens is used in the lens group having a negative refractive power (hereinafter, referred to as 'first arrangement') and an arrangement in which two negative lenses are used in the lens group having a negative refractive power (hereinafter, referred to as 'second arrangement').

Thus, in the basic arrangement, there are two candidates for a location which is favorable for the adjustment of the angle of view. Therefore, it is preferable to select the location at which the adjustment of the angle of view is to be carried out, from the two candidates.

Figure 2A:
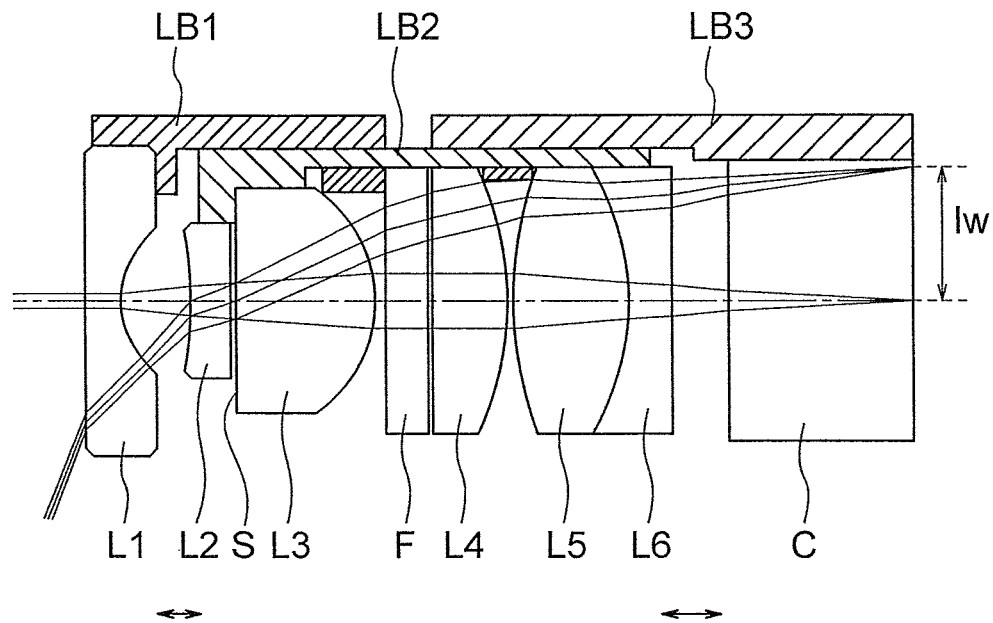
FIG. 2A and FIG. 2B are diagrams showing an endoscope unit according to the present embodiment, where.
Figure 2B:
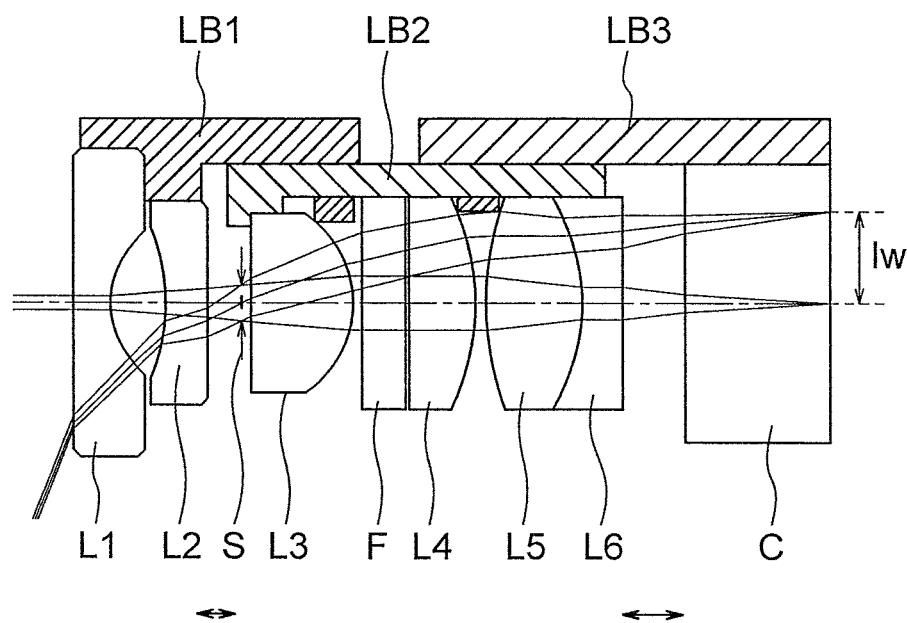

In FIG. 2A and FIG. 2B, an endoscope objective unit according to the present embodiment is shown. FIG. 2A is a diagram showing the first arrangement and FIG. 2B is a diagram showing the second arrangement.

The endoscope objective unit having the first arrangement is shown in FIG. 2A. The endoscope objective unit includes at least an endoscope objective optical system and a lens frame. The endoscope objective optical system includes a negative lens L1, a negative lens L2, a positive lens L3, a positive lens L4, a positive lens L5, and a negative lens L6. The positive lens L5 and the negative lens L6 are cemented.

An aperture stop S is provided to an object-side surface of the positive lens L3. An optical filter F is disposed between the positive lens L3 and the positive lens L4. A glass block C is disposed on an image side of the negative lens L6. The glass block C is a component designed assuming a cover glass of a solid image pickup element. An image-side surface of the glass block C matches with an image pickup surface of an image pickup element. An image of an object with an image height Iw is formed on an image-side surface of the glass block C.

Since an optical system from the negative lens L2 up to the negative lens L6 has an imaging effect, the optical system of this portion inevitably becomes a lens group having a positive refractive power. So, in the first arrangement, the negative lens L1 becomes the front group and lenses from the negative lens L2 up to the negative lens L6 becomes the rear group. Therefore, in the first arrangement, relationship of lens groups peculiar to the retro-focus type is maintained. As a result, a space between the negative lens L1 and the negative lens L2 is a favorable location for the adjustment of the angle of view.

Therefore, in the first arrangement, the negative lens L1 is held by a lens frame LB1, the negative lens L2, the positive lens L3, the optical filter F, the positive lens L4, the positive lens L5, and the negative lens L6 are held by a lens frame LB2, and the glass block C is held by a lens frame LB3.

By making such arrangement, it is possible to move the lens frame LB1 and the lens frame LB2 relatively in a direction along an optical axis. Accordingly, a distance between the negative lens L1 and the negative lens L2, changes. In such manner, in the first arrangement, it is possible to carry out the adjustment of the angle of view by changing the distance between the negative lens L1 and the negative lens L2. Here, the negative lens L1 is the first negative lens and the negative lens L2 is the second negative lens. Therefore, in the first arrangement, it is possible to carry out the adjustment of the angle of view by varying the distance between the first negative lens and the second negative lens.

Moreover, an image position changes when the distance between the negative lens L1 and the negative lens L2 is changed. As aforementioned, the image-side surface of the glass block C matches with the image pickup surface of the image pickup element. Therefore, even when the distance between the negative lens L1 and the negative lens L2 is changed, it is necessary that the image-side surface of the glass block C is let to match with the image position. Therefore, the lens frame LB2 and the lens frame LB3 are to be moved relatively along the optical axis. Accordingly, a distance between the negative lens L6 and the glass block C changes. As a result, it is possible to carry out the adjustment of a focusing position.

The endoscope objective unit having the second arrangement is shown in FIG. 25. The endoscope objective unit includes at least an endoscope objective optical system and a lens frame. The endoscope objective optical system includes a negative lens L1, a negative lens L2, a positive lens L3, a positive lens L4, a positive lens L5, and a negative lens L6. The positive lens L5 and the negative lens L6 are cemented.

An aperture stop S is provided between the negative lens L2 and the positive lens L3. An optical filter F is disposed between the positive lens L3 and the positive lens L4. A glass block C is disposed on an image side of the negative lens L6.

In the second arrangement, a refractive power of the object side across the aperture stop S becomes a negative refractive power, and a refractive power of an image side is a positive refractive power. So, in the second arrangement, the negative lens L1 and the negative lens L2 become the front group and lenses from the negative lens L3 up to the negative lens L6 become the rear group. In such manner, in the second arrangement, a relationship of lens groups peculiar to the retro-focus type is realized precisely. As a result, a space between the negative lens L2 and the aperture stop S is a favorable location for the adjustment of the angle of view.

Therefore, in the second arrangement, the negative lens L1 and the negative lens L2 are held by a lens frame LB1, the positive lens L3, the optical filter F, the positive lens L4, the positive lens L5, and the negative lens L6 are held by a lens frame LB2, and the glass block C is held by a lens frame LB3.

By making such arrangement, it is possible to move the lens frame LB1 and the lens frame LB2 relatively in a direction along an optical axis. Accordingly, a distance between the negative lens L2 and the aperture stop S changes. In such manner, in the second arrangement, it is possible to carry out the adjustment of the angle of view by changing the distance between the second lens L2 and the aperture stop S. Here, the negative lens L2 is the second negative lens. Therefore, in the second arrangement, it is possible to carry out the adjustment of the angle of view by varying the distance between the second negative lens and the aperture stop.

Moreover, an image position changes when the distance between the negative lens L2 and the aperture stop S is changed. As aforementioned, the image-side surface of the glass block C matches with the image pickup surface of the image pickup element. Therefore, even when the distance between the negative lens L2 and the aperture stop S is changed, it is necessary that the image-side surface of the glass block C is let to match with the image position. Therefore, the lens frame LB2 and the lens frame LB3 are to be moved relatively along the optical axis. Accordingly, a distance between the negative lens L6 and the glass block C changes. As a result, it is possible to carry out the adjustment of a focusing position.

Examples of the present invention will be described below. In a lens cross-sectional view of each example, light rays, when an object-side space is let to be water, are shown. Moreover, in each aberration diagram, a horizontal axis indicates an amount of aberration. An aberration curve shown in each aberration diagram indicates aberration at the time of in-water observation. The unit of an amount of spherical aberration and astigmatism is mm. Moreover, the unit of an amount of distortion is %. Furthermore, Iw denotes the maximum image height and the unit thereof is mm, and FNO denotes an F-number. The unit of wavelength of an aberration curve is nm. The spherical aberration is an aberration shown for a d-line.

Example 1

Figure 3A:
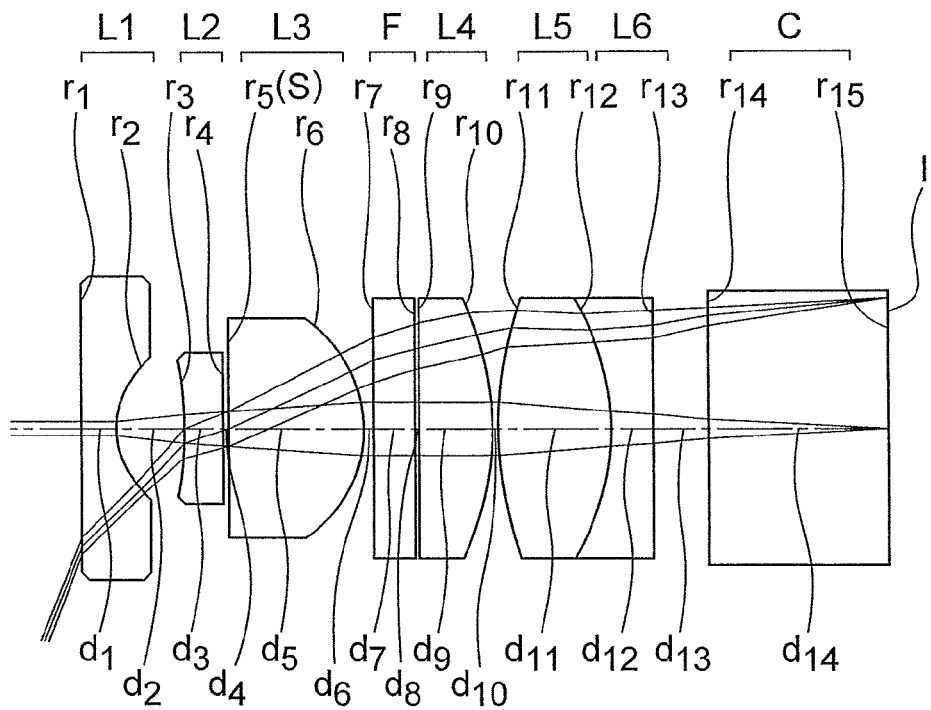
FIG. 3A is a diagram showing a cross-sectional arrangement of an endoscope objective optical system according to an example 1.
Figure 3B:
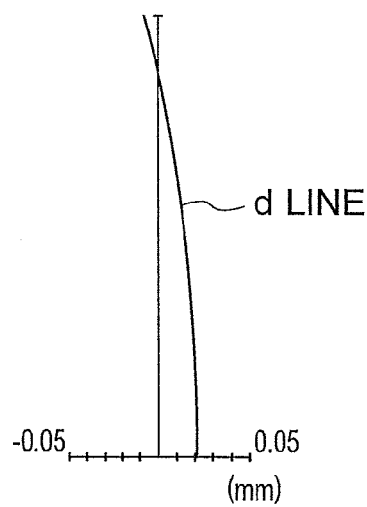
FIG. 3B, FIG. 3C, and FIG. 3D are aberration diagrams showing a spherical aberration (SA), an astigmatism (AS), and a distortion (DT) respectively.
Figure 3C:
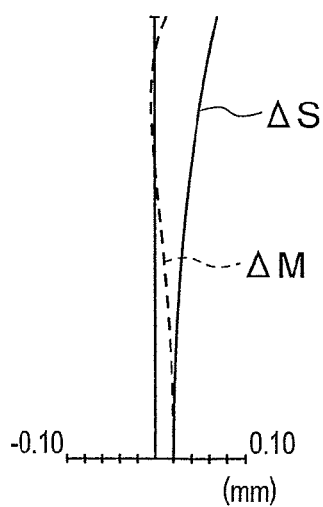
Figure 3D:
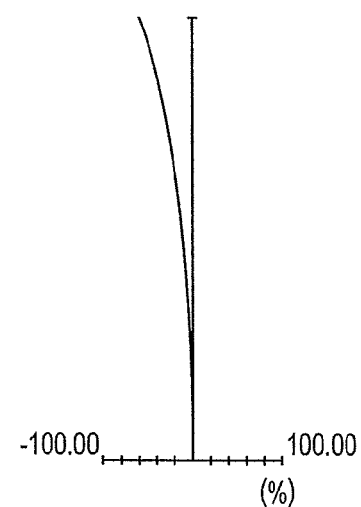

An endoscope objective optical system according to an example 1 will be described below. FIG. 3A, FIG. 3B, FIG. 3C, and FIG. 3D are diagrams showing a cross-sectional arrangement and aberration diagrams respectively of the endoscope objective optical system according to the example 1, where, FIG. 3A shows a lens cross-section, FIG. 3B shows a spherical aberration (SA), FIG. 3C shows an astigmatism (AS), and FIG. 3D shows a distortion (DT).

The endoscope objective optical system according to the example 1, as shown in FIG. 3A, includes in order from an object side, a front group having a negative refractive power, an aperture stop S, and a rear group having a positive refractive power.

The front group includes a planoconcave negative lens L1 of which an object side is a flat surface and a planoconcave negative lens L2 of which an image side is a flat surface.

The rear group includes a planoconvex positive lens L3 of which an object side is a flat surface, a planoconvex positive lens L4 of which an object side is a flat surface, a biconvex positive lens L5, and a planoconcave negative lens L6 of which an image side is a flat surface. Here, the biconvex positive lens L5 and the planoconcave negative lens L6 form a cemented lens having a positive refractive power.

The aperture stop S is provided to an object-side surface of the planoconvex positive lens L3. An optical filter F is disposed in the rear group. The optical filter F is disposed between the planoconvex positive lens L3 and the planoconvex positive lens L4. A glass block C is disposed on an image side of the rear group assuming that a cover glass of a solid image pickup element is disposed.

As aforementioned, for adjusting the variation in the angle of view due to the manufacturing error of components, in the endoscope objective optical system of the example 1, a space between the first negative lens and the second negative lens is let to be the space for adjusting the angle of view, and the optical system is designed such that an adequate adjustment range can be secured. The planoconcave negative lens L1 is the first negative lens and the planoconcave negative lens L2 is the second negative lens. Moreover, a space between the cemented lens and the glass block C is let to be a focus-adjustment space, and the optical system is designed such that an adequate adjustment range can be secured.

An arrangement in which the design is shown by a specific frame structure is shown in FIG. 2A. In the arrangement shown in FIG. 2A, the structure is let to be a 3-body structure with two adjustment spaces as a boundary. Components from the second negative lens up to the cemented lens are disposed in the lens frame LB2. Components from the second negative lens up to the cemented lens, according to an optical conception, can be deemed as a movable group for adjusting the angle of view.

The change in the distance for adjusting the angle of view can be realized by moving relatively the lens frame LB1 and the lens frame LB2 in an optical axial direction. Moreover, the change in the distance for focus adjustment can be realized by moving relatively the lens frame LB2 and the lens frame LB3 in the optical axial direction. Generally, for adjusting the angle of view, the adjustment of the angle of view is to be carried out on the basis of a size of image after a temporary focus adjustment has been carried out. While doing this, smaller the variation in focus better is the workability.

A paraxial lateral magnification of the moving group for adjusting the angle of view in the example 1 is −0.932 times. As it has been widely known according to the optical principle, the paraxial lateral magnification of a significant point where there is no variation in focus is −1 times. The paraxial lateral magnification in the example 1 is close to the paraxial lateral magnification of the significant point where there is no variation in focus. Therefore, in the example 1, the variation in focus resulting from the adjustment of the angle of view is small. Thus, in the example 1, a consideration is given at the time of designing the optical system, such that the variation in focus while adjusting the angle of view becomes small.

Characteristics of the first negative lens will be described below. In the first negative lens, the object-side surface is let to be a flat surface. This structure is common as a front-end structure of endoscope. Generally, in a super-wide angle lens and a fish-eye lens, an object-side surface is a convex surface. When an object-side surface is let to be a convex surface in an endoscope, since illuminating light is incident directly, it is necessary to devise a light-shielding structure at a front-end portion of endoscope. Therefore, in the example 1, it is not necessary to devise an idea for shielding light in the first negative lens and the frame structure with respect to a flare of light incident directly from an illuminating system not shown in the diagram.

Moreover, since there is no bulge as the object-side surface of the first negative lens is flat, even when an object hits from the object side, the probability of the first negative lens getting a scratch is lower than that in a case of a convex surface. It is preferable to let a material of the first negative lens to be sapphire which has a superior mechanical durability. When the first negative lens is made of sapphire, even as a material, it cannot get a scratch easily. Moreover, by metalizing an outer circumference of sapphire and soldering it to the lens frame LB1, it is possible to provide a lens-frame structure with an extremely high reliability.

The endoscope objective optical system according to the example 1 generally has an angle of view by which it may be classified as a fish-eye lens. In spite of this, since an outer diameter of the first negative lens is 2.2 mm which is extremely small, no strain is imposed on a structural design of the front-end of endoscope.

By using a material having a high refractive index for the second negative lens, an absolute value of a negative Petzval sum is let to be as small as possible. Moreover, in the second negative lens, an aperture-stop side is let to be a flat surface. When the aperture-stop side is let to be a flat surface, in a case in which the aperture stop includes a thin plate, the aperture stop can be pinched between the second negative lens and the first positive lens. Thus, by letting the structure such that the aperture stop can be pinched in a gap between the two lenses, an air space is reduced. Reducing the air space other than an optical adjustment space leads to securing a favorable lens workability (avoiding deterioration of workability resulting from thinning) and contributes to shortening the overall length of the optical system.

By using a material having a low refractive index for the first positive lens, a positive Petzval sum is let to be large. In the first positive lens, an image-side surface is a convex surface directed toward the image side. Thus, regarding the first positive lens, a design in which an angle of refraction of a principal ray at the image-side surface becomes small, or a so-called concentric design, is possible. For making the positive Petzval sum for the first positive lens large, the refractive index is to be made low while imparting a large positive refractive power. However, when such an arrangement is made, since a radius of curvature of the lens surface becomes small, an aberration is susceptible to occur. At the same time, the first positive lens has a concentric design. Therefore, in the first positive lens, even when the radius of curvature is made small, it is possible to suppress a fluctuation in astigmatism due to decentering.

The positive Petzval sum is ingenerated in the second positive lens as well. However, in the second positive lens, since priority is given to lowering a height of a light ray rather than increasing the Petzval sum, a material having a high refractive index is used for the second positive lens. In the second positive lens, the height of a light ray is higher than that in the first positive lens. Therefore, an on-axis lens thickness and the refractive power of the image-side convex surface in the second positive lens have an effect on an outer diameter of the second positive lens onward.

In the second positive lens, the image-side surface is a convex surface directed toward the image side. Even for the second positive lens, a comparatively concentric design is possible, thereby making it easy to strengthen the positive refractive power. Therefore, by bringing the convex surface of the image-side surface as close as possible to the first positive lens paraxially, it is possible to lower the height of a light ray on the image side of the second positive lens.

In the second positive lens, as the refractive index is made higher, the radius of curvature increases. With the increase in the radius of curvature, it is possible to make the on-axis lens thickness thin. Furthermore, since an effect of length reduction in an air conversion lens is also achieved, the paraxial refractive power is brought closer to the refractive power of the first positive lens.

The cemented lens includes a positive lens of a material having a low refractive index and a negative lens of a material having a high refractive index. Therefore, by imparting a negative refractive power to a cemented surface, the astigmatism and the coma are corrected. By securing a large difference in a refractive index of an object side of the cemented surface and a refractive index of an image side of the cemented surface, an arrangement is made such that a radius of curvature of the cemented surface does not become excessively small. Accordingly, the aberration fluctuation resulting from decentering is suppressed. On the object side of the cemented lens, there is no lens that is capable of correcting a chromatic aberration of magnification. Therefore, an ultra-high dispersion glass is used for the negative lens in the cemented lens, and the chromatic aberration of magnification is corrected collectively.

The optical filter F is a filter such as a color correction filter. The color correction filter includes an absorbent material which attenuates from a long-wavelength side of a visible range up to a near-infrared region. However, in a urinary-organ application, sometimes an Nd:YAG (Neodymium Yttrium Aluminum Garnet) laser is used for treatment of a tumor etc. Therefore, a multilayer optical interference film having almost 100% reflectance for a wavelength of the Nd:YAG laser may be applied to either one surface or both surfaces of the color correction filter.

Since the multilayer optical interference film has a strong dependence on an angle of incidence, the reflectance changes substantially according to the angle of incidence. Therefore, in a case in which the color correction filter includes the multilayer optical interference film, it is necessary to dispose the color correction filter at a location where an angle of incidence of the principal ray does not become excessively large. In the arrangement of the endoscope objective optical system according to the example 1, it is desirable that the color correction filter is disposed on the image side of the first positive lens.

Specifications of the endoscope objective optical system according to the example 1 will be described below. In the endoscope objective optical system according to the example 1, the maximum image height Iw in the in-water observation state is 0.942 mm. The maximum image height Iw is assumed to be in accord with an effective image pickup area of the solid image pickup element. Therefore, in the in-water observation state, the entire effective image pickup area of the solid image pickup element is used.

Moreover, in the endoscope objective optical system according to the example 1, the in-water angle of view is 138.0°. Therefore, the endoscope objective optical system according to the example 1, as an endoscope objective optical system which enables in-water observation, is an extremely wide-angle optical system. According to the endoscope objective optical system of the example 1, it is possible to observe an object in water by using the entire effective image pickup area of the solid image pickup element.

In the endoscope objective optical system according to the example 1, since the object-side surface of the first negative lens is a flat surface, no light ray except for a light ray with the angle of view in air of up to 180° can be incident on the first negative lens. When the maximum image height at the angle of view in air of 180° is let to be Ia, the in-water angle of view of a light ray forming an image at a position of Ia becomes 97.2°. It is obvious that a relation of Ia and Iw from the in-water angle of view is indicated by the following expression.

$$Ia \text{ (in-water angle of view 97.2°)} < Iw \text{ (in-water angle of view 138.0°)}$$

Figure 6A:
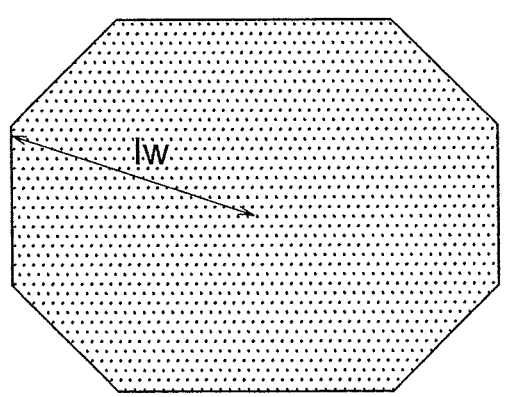
FIG. 6A and FIG. 6B are conceptual diagrams showing an image pickup range, where.
Figure 6B:
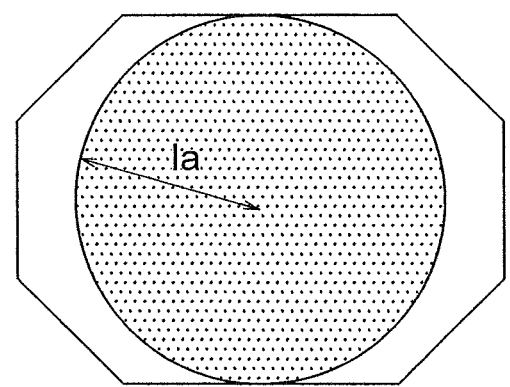

FIG. 6A and FIG. 6B are conceptual diagrams showing an image pickup range, where, FIG. 6A is a diagram showing an image pickup range in the in-water observation state and FIG. 6B is a diagram showing an image pickup range in the state of observation in air. In FIG. 6A and FIG. 6B, it is illustrated diagrammatically to understand intuitively that the image pickup range in the state of observation in air becomes narrower than the image pickup range in the in-water observation state.

Here, it is assumed that an electrical field mask having octagonal shape is to be put on the effective image pickup area of the solid image pickup element. In this case, since the effective image pickup area is at an inner side of an area shown by the octagonal shape, the image pickup range is also at the inner side of the area shown by the octagonal shape. In FIG. 6A and FIG. 6B, the image pickup range is hatched.

FIG. 6A shows an image pickup range in the in-water observation state. As shown in FIG. 6A, in the in-water observation state, the entire inner side of the area shown by the octagonal shape becomes the image pickup area. Therefore, in the in-water observation state, the entire effective image pickup area can be used. Moreover, the image pickup range is the range indicated by the octagonal shape. Therefore, the maximum image height Iw is the maximum of lengths connecting a center of the octagonal shape to sides of the octagonal shape.

FIG. 6B shows an image pickup range in the state of observation in air. As shown in FIG. 6B, in the state of observation in air, an area shown by a circle in an area shown by the octagonal shape becomes the image pickup range.

Therefore, in the state of observation in air, the whole of the effective image pickup area is not used for image pickup. Moreover, the image pickup range is the area shown by the circle. Therefore, a radius of the circle becomes the maximum image height Ia. An area at an outer side of the circle is not hatched. Since an object-image is not formed in this area, this area becomes an optically ineffective area.

Example 2

Figure 4A:
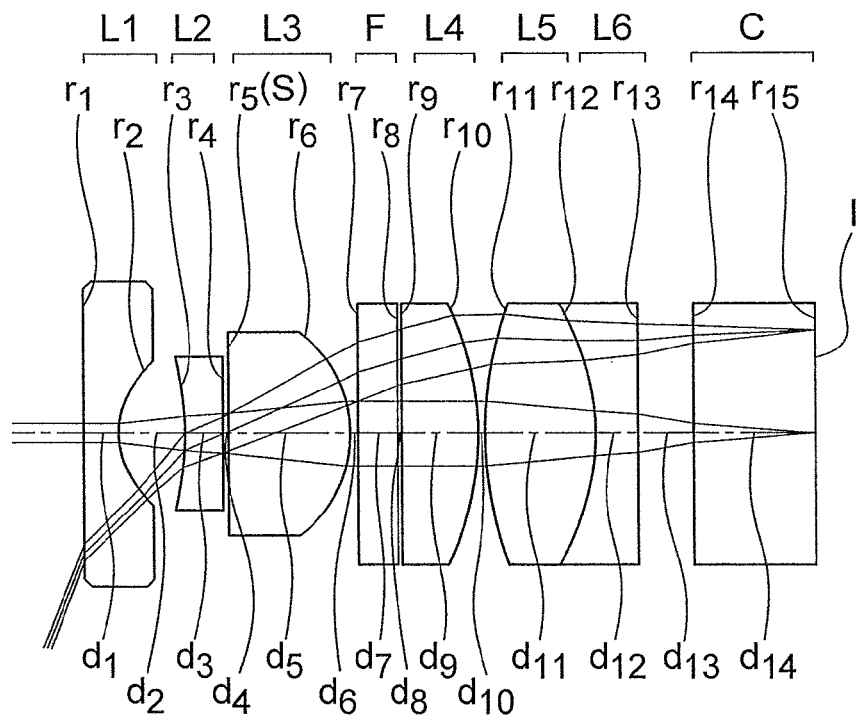
FIG. 4A is a diagram showing a cross-sectional arrangement of an endoscope objective optical system according to an example 2.
Figure 4B:
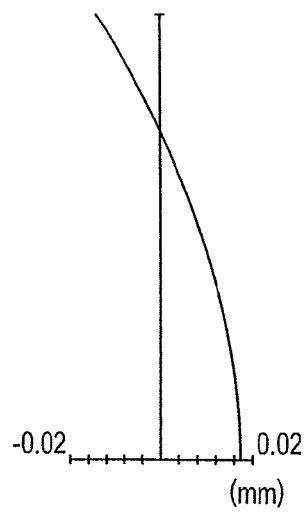
FIG. 4B, FIG. 4C, and FIG. 4D are aberration diagrams showing a spherical aberration (SA), an astigmatism (AS), and a distortion (DT) respectively.
Figure 4C:
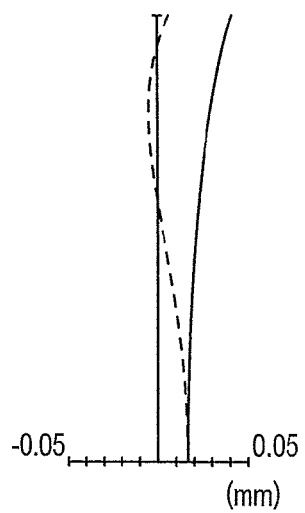
Figure 4D:
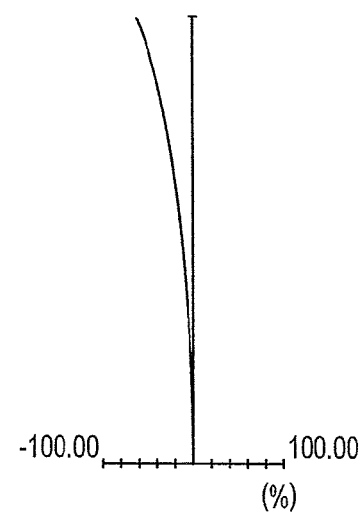

An endoscope objective optical system according to an example 2 will be described below. FIG. 4A, FIG. 4B, FIG. 4C, and FIG. 4D are diagrams showing a cross-sectional arrangement and aberration diagrams respectively of the endoscope objective optical system according to the example 2, where, FIG. 4A shows a lens cross-section, FIG. 4B shows a spherical aberration (SA), FIG. 4C shows an astigmatism (AS), and FIG. 4D shows a distortion (DT).

The endoscope objective optical system according to the example 2, as shown in FIG. 4A, includes in order from an object side, a front group having a negative refractive power, an aperture stop S, and a rear group having a positive refractive power.

The front group includes a planoconcave negative lens L1 of which an object side is a flat surface and a planoconcave negative lens L2 of which an image side is a flat surface.

The rear group includes a planoconvex positive lens L3 of which an object side is a flat surface, a planoconvex positive lens L4 of which an object side is a flat surface, a biconvex positive lens L5, and a planoconcave negative lens L6 of which an image side is a flat surface. Here, the biconvex positive lens L5 and the planoconcave negative lens L6 form a cemented lens having a positive refractive power.

The aperture stop S is provided to an object-side surface of the planoconvex positive lens L3. An optical filter F is disposed in the rear group. The optical filter F is disposed between the planoconvex positive lens L3 and the planoconvex positive lens L4. A glass block C is disposed on an image side of the rear group assuming that a cover glass of a solid image pickup element is disposed.

Similarly as in the example 1, it is assumed to be combined with the solid image pickup element even in the example 2. However, a size of the solid image pickup element assumed in the example 2 is smaller than a size of the solid image pickup element assumed in the example 1. Therefore, in the example 2, the optical system is designed by setting the maximum image height Iw to be smaller than the maximum image height in the example 1.

With the maximum image height made smaller, it is necessary to make a spot size of a diffraction image small. For making the spot size of the diffraction image small, in the example 2, the F-number is made smaller than the F-number in the example 1.

Similarly as in the example 1, since the type of lenses in the example 2 is not that sensitive to a difference in the size of the solid image pickup element and a difference in the F-number, there is some degree of versatility.

As aforementioned, for adjusting the variation in the angle of view due to the manufacturing error of components, in the endoscope objective optical system of the example 2, the space between the first negative lens and the second negative lens is let to be the space for the adjustment of the angle of view, and the optical system is designed such that sufficient adjustment range can be secured. The planoconcave negative lens L1 is the first negative lens and the planoconcave negative lens L2 is the second negative lens. Moreover, a space between the cemented lens and the glass block C is let to be a focus-adjustment space, and the optical system is designed such that an adequate adjustment range can be secured.

A specific frame structure in the example 2 is same as the specific frame structure in the example 1.

As aforementioned, in the example 2, the space between the first negative lens and the second negative lens is let to be the space for the adjustment of the angle of view. The paraxial lateral magnification of the group to be moved for the adjustment of the angle of view in this case is −0.754 times. When compared with an absolute value, the value of the paraxial lateral magnification in the example 2 has become smaller than the value of the paraxial lateral magnification in the example 1. The reason for this is that in the example 2, the maximum image height Iw became smaller as compared to that in the example 1. As a result, in the example 2, the paraxial lateral magnification has become smaller as compared to that in the example 1.

Here, supposedly, when the space for the adjustment of the angle of view is let to be a space between the second negative lens and the aperture stop, the paraxial lateral magnification from the aperture stop up to the cemented lens becomes −1.131 times. As aforementioned, at the significant point where there is no variation in focus, the paraxial lateral magnification becomes −1 times. Closer to the paraxial later magnification at the significant point is a case in which the space for the adjustment of the angle of view is let to be a space between the second negative lens and the aperture stop. Therefore, in the example 2, it is possible to let the space between the second negative lens and the aperture stop to be the space for adjustment of the angle of view.

Example 3

Figure 5A:
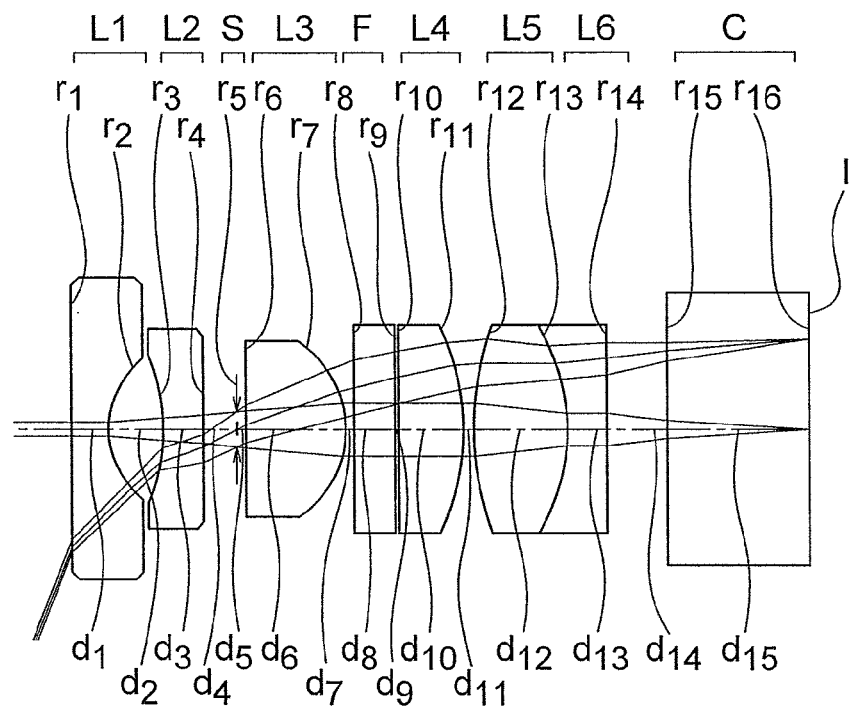
FIG. 5A is a diagram showing a cross-sectional arrangement of an endoscope objective optical system according to an example 3.
Figure 5B:
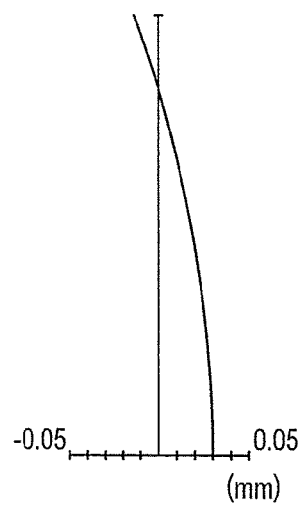
FIG. 5B, FIG. 5C, and FIG. 5D are aberration diagrams showing a spherical aberration (SA), an astigmatism (AS), and a distortion (DT) respectively.
Figure 5C:
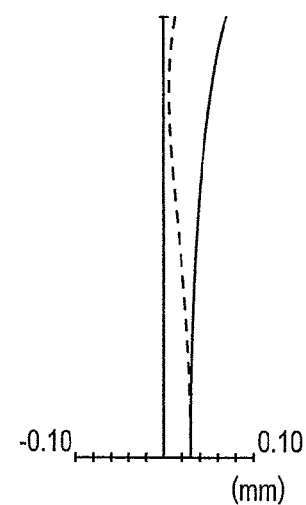
Figure 5D:
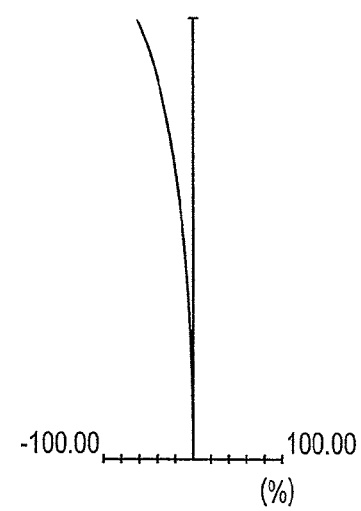

An endoscope objective optical system according to an example 3 will be described below. FIG. 5A, FIG. 5B, FIG. 5C, and FIG. 5D are diagrams showing a cross-sectional arrangement and aberration diagrams respectively of the endoscope objective optical system according to the example 3, where, FIG. 5A shows a lens cross-section, FIG. 5B shows a spherical aberration (SA), FIG. 5C shows an astigmatism (AS), and FIG. 5D shows a distortion (DT).

The endoscope objective optical system according to the example 3, as shown in FIG. 5A, includes in order from an object side, a front group having a negative refractive power, an aperture stop S, and a rear group having a positive refractive power.

The front group includes a planoconcave negative lens L1 of which an object side is a flat surface and a planoconcave negative lens L2 of which an image side is a flat surface.

The rear group includes a planoconvex positive lens L3 of which an object side is a flat surface, a planoconvex positive lens L4 of which an object side is a flat surface, a biconvex positive lens L5, and a negative meniscus lens L6 having a convex surface directed toward an image side. Here, the biconvex positive lens L5 and the negative meniscus lens L6 form a cemented lens having a positive refractive power.

The aperture stop is provided between the planoconcave negative lens L2 and the planoconvex positive lens L3. An optical filter F is disposed in the rear group. The optical filter F is disposed between the planoconvex positive lens L3 and the planoconvex positive lens L4. A glass block C is disposed on an image side of the rear group assuming that a cover glass of a solid image pickup element is disposed.

Similarly as in the example 1, it is assumed to be combined with the solid image pickup element even in the example 3. However, a size of the solid image pickup element assumed in the example 3 is further smaller than the size of the solid image pickup element assumed in the example 2. Therefore, in the example 3, the optical system is designed by setting the maximum image height Iw to be smaller than the maximum image height in the example 2.

As aforementioned, for adjusting the variation in the angle of view due to the manufacturing error of components, in the endoscope objective optical system of the example 3, the space between the second negative lens and the aperture stop is let to be the space for the adjustment of the angle of view, and the optical system is designed such that an adequate adjustment range can be secured. The planoconcave negative lens L2 is the second negative lens. Moreover, a space between the cemented lens and the glass block C is let to be a focus-adjustment space, and the optical system is designed such that an adequate adjustment range can be secured.

An arrangement in which this design is shown by a specific frame structure is shown in FIG. 2B. In the arrangement shown in FIG. 2B, the structure is let to be a 3-body structure with two adjustment spaces as a boundary. Components from the first positive lens up to the cemented lens are disposed in the lens frame LB2. Components from the first positive lens up to the cemented lens, according to an optical conception, can be deemed as a moving group for adjusting the angle of view.

The change in the distance for adjusting the angle of view can be realized by moving relatively the lens frame LB1 and the lens frame LB2 in an optical axial direction. Moreover, the change in the adjusting for the focus adjustment can be realized by moving relatively the lens frame LB2 and the lens frame LB3 in the optical axial direction.

In the example 3, a space between the second negative lens and the aperture stop is let to be the space for the adjustment of the angle of view. A paraxial lateral magnification of the moving group for adjusting the angle of view in this case is −1.255 times. Here, supposedly, when the space for the adjustment of the angle of view is let to be a space between the first negative lens and the second negative lens, the paraxial lateral magnification from the second negative lens up to the cemented lens becomes −0.678 times. As aforementioned, at the significant point where there is no variation in focus, the paraxial lateral magnification becomes −1 times. Closer to the paraxial lateral magnification at the significant point is a case in which the space for the adjustment of the angle of view is let to be a space between the second negative lens and the aperture stop. Therefore, in the example 3, the space between the second negative lens and the aperture stop is let to be a location for the adjustment of the angle of view.

With regard to only the paraxial lateral magnification, when the maximum image height Iw is comparatively small, it is desirable to let the space between the second negative lens and the aperture stop to be the space for the adjustment of the angle of view as in the example 3. On the other hand, when the maximum image height Iw is comparatively large, it is desirable to let the space between the first negative lens and the second negative lens to be the space for the adjustment of the angle of view as in the example 1. However, changing the distance for adjusting the angle of view is related not only to the variation in focus but also to aberration fluctuation and restriction on the frame structure. Therefore, a judgment is to be made in a comprehensive manner and an appropriate space is to be selected.

Numerical data of each example described above is shown below. In symbols, r denotes radius of curvature of each lens surface, d denotes a distance between respective lens surfaces, nd denotes a refractive index of each lens for d-line, νd denotes an Abbe number for each optical element, ft denotes a focal length of the overall endoscope objective optical system Fno denotes an F number, D0w denotes an object distance, Iw denotes a maximum image height, ωW denotes a half angle of view. Numerical data of each Do, Iw and ωW is envisaged for in-water observation. Moreover, each unit of r, d, ft, D0w, Iw, Lt, Laf, ΣLa is mm, and unit of ωW is ° (degree).

Example 1

Unit mm

Surface data

| Surface no. | r | d | nd | νd |
|---|---|---|---|---|
| 1 | ∞ | 0.25 | 1.76820 | 71.7 |
| 2 | 0.639 | 0.49 | | |
| 3 | −3.157 | 0.30 | 2.00330 | 28.27 |
| 4 | ∞ | 0.03 | | |
| 5(Stop) | ∞ | 1.00 | 1.58913 | 61.14 |
| 6 | −0.961 | 0.08 | | |
| 7 | ∞ | 0.30 | 1.52100 | 65.13 |
| 8 | ∞ | 0.03 | | |
| 9 | ∞ | 0.52 | 1.88300 | 40.76 |
| 10 | −2.484 | 0.05 | | |
| 11 | 2.665 | 0.83 | 1.58913 | 61.14 |
| 12 | −1.869 | 0.30 | 1.95906 | 17.47 |
| 13 | ∞ | 0.42 | | |
| 14 | ∞ | 1.30 | 1.51633 | 64.14 |
| 15(Image plane) | ∞ | | | |

Various data

| ft | 0.717 |
|---|---|
| FNO. | 5.528 |
| D0w | 8.5 |
| Iw | 0.942 |
| 2ωw | 138.0 |
| Lt | 5.90 |
| Lsf | 1.07 |
| ΣLa | 0.52 |

Example 2

Unit mm

Surface data

| Surface no. | r | d | nd | νd |
|---|---|---|---|---|
| 1 | ∞ | 0.25 | 1.76820 | 71.79 |
| 2 | 0.639 | 0.49 | | |
| 3 | −2.461 | 0.30 | 2.00330 | 28.27 |
| 4 | ∞ | 0.03 | | |
| 5(Stop) | ∞ | 0.91 | 1.58913 | 61.14 |
| 6 | −0.978 | 0.08 | | |
| 7 | ∞ | 0.30 | 1.52100 | 65.13 |
| 8 | ∞ | 0.03 | | |
| 9 | ∞ | 0.56 | 1.88300 | 40.76 |
| 10 | −2.107 | 0.05 | | |
| 11 | 2.526 | 0.82 | 1.69680 | 55.53 |
| 12 | −1.667 | 0.30 | 1.95906 | 17.47 |
| 13 | ∞ | 0.44 | | |
| 14 | ∞ | 0.90 | 1.51633 | 64.14 |
| 15(Image plane) | ∞ | | | |

Example 3

| | Unit mm | | | |
|---|---|---|---|---|
| | Surface data | | | |
| Surface no. | r | d | nd | vd |
| 1 | ∞ | 0.25 | 1.76820 | 71.79 |
| 2 | 0.639 | 0.41 | | |
| 3 | −1.354 | 0.30 | 2.00330 | 28.27 |
| 4 | ∞ | 0.25 | | |
| 5(Stop) | ∞ | 0.06 | | |
| 6 | ∞ | 0.72 | 1.58144 | 40.75 |
| 7 | −0.874 | 0.08 | | |
| 8 | ∞ | 0.30 | 1.52100 | 65.13 |
| 9 | ∞ | 0.03 | | |
| 10 | ∞ | 0.49 | 1.77250 | 49.60 |
| 11 | −1.869 | 0.05 | | |
| 12 | 2.256 | 0.71 | 1.58913 | 61.14 |
| 13 | −1.345 | 0.30 | 1.95906 | 17.47 |
| 14 | −22.300 | 0.42 | | |
| 15 | ∞ | 1.05 | 1.51633 | 64.14 |
| 16(Image plane) | ∞ | | | |

| Various data | |
|---|---|
| ft | 0.525 |
| FNO. | 4.761 |
| D0w | 8.5 |
| Iw | 0.652 |
| 2ωw | 138.1 |
| Lt | 5.42 |
| Lsf | 1.21 |
| ΣLa | 0.66 |

The values of Petzval sum which is multiplied by ft are shown below.

| | Example1 | Example2 | Example3 |
|---|---|---|---|
| first negative lens | −0.487 | −0.397 | −0.357 |
| second negative lens | −0.114 | −0.119 | −0.194 |
| first positive lens | 0.276 | 0.221 | 0.221 |
| second positive lens | 0.135 | 0.130 | 0.123 |
| Cemented lens | 0.054 | 0.067 | 0.051 |

Next, the values of conditional expressions (1) to (15) in each example of the objective optical system are shown below.

| Conditional Expression | Example1 | Example2 | Example3 |
|---|---|---|---|
| (1)Iw/ft | 1.31 | 1.29 | 1.24 |
| (2)Lt/Iw | 6.26 | 7.27 | 8.31 |
| (3)Lsf/ft | 1.49 | 1.83 | 2.30 |
| (4)ΣLa/Lsf | 0.49 | 0.49 | 0.55 |
| (5)PSp12 × ft | 0.411 | 0.351 | 0.344 |
| (6)|PSp12/PSn12| | 0.684 | 0.680 | 0.624 |
| (7)PS3 × ft | 0.054 | 0.067 | 0.051 |

According to the present invention, it is possible to provide an endoscope objective optical system having a thin diameter, a wide in-water angle of view, a small variation in the angle of view, and a short overall length of the optical system.

In such manner, the present invention is useful for an endoscope objective optical system having a thin diameter, a wide in-water angle of view, a small variation in the angle of view, and a short overall length.

What is claimed is:

1. An endoscope objective optical system, comprising in order from an object side:
   a front group having a negative refractive power;
   an aperture stop; and
   a rear group having a positive refractive power, wherein the front group includes a first negative lens and a second negative lens, and
   the following conditional expressions (1), (2), (3'), and (4) are satisfied:

$$1 < Iw/ft < 1.8 \quad (1)$$

$$4 < Lt/Iw < 9.5 \quad (2),$$

$$1.49 \leq Lsf/ft \leq 2.30 \quad (3'), \text{ and}$$

$$0.38 < \Sigma La/Lsf < 0.6 \quad (4)$$

where,
Iw denotes a maximum image height,
ft denotes a focal length of the overall endoscope objective optical system,
Lt denotes an overall length of the endoscope objective optical system,
Lsf denotes a distance from an object-side first surface up to the aperture stop, and
ΣLa denotes a sum of air spaces between the object-side first surface and the aperture stop, and in this case,
the overall length is a distance from the object-side first surface up to an image position, and
the object-side first surface is a lens surface positioned nearest to object in the endoscope objective optical system.

2. The endoscope objective optical system according to claim 1, wherein
the rear group includes on the object side a first positive lens and a second positive lens, and
the following conditional expressions (5) and (6) are satisfied:

$$0.25 < PSp12 \times ft \quad (5), \text{ and}$$

$$0.5 < |PSp12/PSn12| < 1.1 \quad (6)$$

where,
ft denotes the focal length of the overall endoscope objective optical system,
PSp12 denotes Petzval sum for the first positive lens and the second positive lens, and
PSn12 denotes Petzval sum for the first negative lens and the second negative lens.

3. The endoscope objective optical system according to claim 2, wherein
the rear group has a cemented lens on an image side of the second positive lens, and
the cemented lens includes a lens having a positive refractive power and a lens having a negative refractive power, and
the following conditional expression (7) is satisfied:

$$0.02 < PS3 \times ft \quad (7)$$

where,
ft denotes the focal length of the overall endoscope objective optical system, and
PS3 denotes Petzval sum for the cemented lens.

4. An endoscope objective optical system, comprising in order from an object side:
a front group having a negative refractive power;
an aperture stop; and
a rear group having a positive refractive power, wherein
the front group includes a first negative lens and a second negative lens, and
the rear group includes a first positive lens, a second positive lens, and a cemented lens, and
the cemented lens includes a lens having a positive refractive power and a lens having a negative refractive power, and
the following conditional expressions (1), (2), (3'), and (4) are satisfied:

$$1 < Iw/ft < 1.8 \quad (1),$$

$$4 < Lt/Iw < 9.5 \quad (2),$$

$$1.49 \leq Lsf/ft < 2.30 \quad (3'), \text{ and}$$

$$0.38 < \Sigma La/Lsf < 0.6 \quad (4)$$

where,
Iw denotes a maximum image height,
ft denotes a focal length of the overall endoscope objective optical system,
Lt denotes an overall length of the endoscope objective optical system,
Lsf denotes a distance from an object-side first surface up to the aperture stop, and
ΣLa denotes a sum of air spaces between the object-side first surface and the aperture stop, and in this case,
the overall length is a distance from the object-side first surface up to an image position, and
the object-side first surface is a lens surface positioned nearest to object in the endoscope objective optical system.

5. An endoscope objective optical system, comprising in order from an object side:
a front group having a negative refractive power;
an aperture stop; and
a rear group having a positive refractive power, wherein
the front group includes a first negative lens and a second negative lens,
the rear group includes a first positive lens, a second positive lens, and a cemented lens,
the cemented lens includes a lens having a positive refractive power and a lens having a negative refractive power, and
the following conditional expressions (1), (2), (3), (4), (5), (6), and (7) are satisfied:

$$1 < Iw/ft < 1.8 \quad (1),$$

$$4 < Lt/Iw < 9.5 \quad (2),$$

$$Lsf/ft \leq 2.8 \quad (3),$$

$$0.38 < \Sigma La/Lsf < 0.6 \quad (4)$$

$$0.25 < PSp12 \times ft \quad (5),$$

$$0.5 < |PSp12/PSn12| < 1.1 \quad (6), \text{ and}$$

$$0.02 < PS3 \times ft \quad (7)$$

where,
Iw denotes a maximum image height,
ft denotes a focal length of the overall endoscope objective optical system,
Lt denotes an overall length of the endoscope objective optical system,
Lsf denotes a distance from an object-side first surface up to the aperture stop, and
ΣLa denotes a sum of air spaces between the object-side first surface and the aperture stop, and in this case,
the overall length is a distance from the object-side first surface up to an image position, and
the object-side first surface is a lens surface positioned nearest to object in the endoscope objective optical system,
PSp12 denotes Petzval sum for the first positive lens and the second positive lens,
PSn12 denotes Petzval sum for the first negative lens and the second negative lens, and
PS3 denotes Petzval sum for the cemented lens.

6. An endoscope objective optical system, comprising in order from an object side:
a front group having a negative refractive power;
an aperture stop; and
a rear group having a positive refractive power, wherein
the front group includes a first negative lens and a second negative lens,
the rear group includes a first positive lens, a second positive lens, and a cemented lens,
the cemented lens includes a lens having a positive refractive power and a lens having a negative refractive power,
the following conditional expressions (1), (2), (3), and (4) are satisfied, and
a refractive index of the second negative lens is not less than 1.75:

$$1 < Iw/ft < 1.8 \quad (1),$$

$$4 < Lt/Iw < 9.5 \quad (2),$$

$$Lsf/ft \leq 2.8 \quad (3), \text{ and}$$

$$0.38 < \Sigma La/Lsf < 0.6 \quad (4)$$

where,
Iw denotes a maximum image height,
ft denotes a focal length of the overall endoscope objective optical system,
Lt denotes an overall length of the endoscope objective optical system,
Lsf denotes a distance from an object-side first surface up to the aperture stop, and
ΣLa denotes a sum of air spaces between the object-side first surface and the aperture stop, and in this case,
the overall length is a distance from the object-side first surface up to an image position, and the object-side first surface is a lens surface positioned nearest to object in the endoscope objective optical system.

7. An endoscope objective optical system, comprising in order from an object side:

a front group having a negative refractive power;

an aperture stop; and a rear group having a positive refractive power, wherein the front group includes a first negative lens and a second negative lens, the rear group includes a first positive lens, a second positive lens, and a cemented lens, the cemented lens includes a lens having a positive refractive power and a lens having a negative refractive power, the following conditional expressions (1), (2), (3), and (4) are satisfied, and a refractive index of the second positive lens is higher than the refractive index of the first positive lens:

$$1 < Iw/ft < 1.8 \quad (1),$$

$$4 < Lt/Iw < 9.5 \quad (2),$$

$$Lsf/ft < 2.8 \quad (3), \text{ and}$$

$$0.38 < \Sigma La/Lsf < 0.6 \quad (4)$$

where,

Iw denotes a maximum image height, ft denotes a focal length of the overall endoscope objective optical system, Lt denotes an overall length of the endoscope objective optical system, Lsf denotes a distance from an object-side first surface up to the aperture stop, and ΣLa denotes a sum of air spaces between the object-side first surface and the aperture stop, and in this case, the overall length is a distance from the object-side first surface up to an image position, and the object-side first surface is a lens surface positioned nearest to object in the endoscope objective optical system.

* * * * *